United States Patent [19]

Yatabe

[11] 4,100,678
[45] Jul. 18, 1978

[54] METAL BRACKET FOR USE IN ORTHODONTIC TREATMENT

[76] Inventor: Kenichi Yatabe, 1-5, 4-Chome Shimo Meguro, Meguro-Ku, Tokyo, Japan

[21] Appl. No.: 733,486

[22] Filed: Oct. 18, 1976

[30] Foreign Application Priority Data

Oct. 20, 1975 [JP] Japan .......................... 50-142657[U]

[51] Int. Cl.² ............................................... A61C 7/00
[52] U.S. Cl. .................................................. 32/14 A
[58] Field of Search .......................... 51/319; 32/14 A

[56] References Cited

U.S. PATENT DOCUMENTS

| | | | |
|---|---|---|---|
| 3,765,091 | 10/1973 | Northcutt | 32/14 A |
| 3,932,940 | 1/1976 | Andren | 32/14 A |

*Primary Examiner*—Robert Peshock
*Attorney, Agent, or Firm*—H. Ross Workman; J. Winslow Young

[57] ABSTRACT

A metal bracket for use in orthodontic treatment is provided which comprises a bracket body for receiving and securing a wire which transmits orthodontic force to the tooth and a support base for supporting said bracket body. A plurality of fine pores in the form of undercut is formed by subjecting the base to sand-blasting treatment and then to etching process. Such metal brackets have strong adhesion to the teeth.

4 Claims, 4 Drawing Figures

METAL BRACKET FOR USE IN ORTHODONTIC TREATMENT

BACKGROUND OF THE INVENTION

1. Field of the Invention

This invention relates to an orthodontic appliance, and more particularly to a metal bracket for receiving a wire which transmits orthodontic force to the tooth to which the bracket adheres.

2. Prior Art

In general a metal bracket of the type above referred to comprises a bracket body for receiving and securing the wire and a support base for supporting the body, said support base being bonded to the tooth with an adhesive. Hithertofore, the base has been modified in various ways to give strong adhesion between the base and the tooth.

A metal bracket of one conventional type comprises a support base having a plurality of through-pores, each spaced at constant intervals along the periphery of the base. A metal bracket similar to this type comprises a support base having a plurality of through-pores not only at its periphery but also within its whole region. In either case an adhesive applied to the back side of the base partly comes out through the through-pores at the periphery of the base and solidifies on its surface, thereby providing strong adhesion in addition to the bonding between the back side of the base and the tooth. This type of the bracket, however, has a disadvantage that when brushing the tooth the adhesive on the surface of the support base is gradually abrased and finally worn out so that the metal bracket is detached off the tooth.

As another known type of the metal bracket, instead of the support base of metal plate a net made of metal is secured to a bracket body. However, it happens that the net often gets unknitted in its circumference and consequently the adhesion between the net and the tooth becomes lower. As a modified type, the metal net is provided under the thin metal plate support base. It, however, costs high since additional process is required for the production. Furthermore, the modified bracket becomes thick in its height so that it is not comfortable for patients.

OBJECTS AND SUMMARY OF THE INVENTION

It is an object of the present invention to provide a metal bracket which can be used for a long perod of time.

It is another object of the invention to provide a metal bracket which can be firmly adhered to the tooth and which is not detached off the tooth when brushing the tooth. It is a further object of the invention to provide a metal bracket which can be produced in a simple way and which is cheap.

The other objects of the present invention will become apparent from the following description.

A metal bracket according to the present invention comprises a bracket body for receiving and securing a wire which transmits orthodontic force to the tooth and a support base for supporting the body and which is adhered to the tooth, a plurality of fine pores in the form of undercut being formed in the support base. The term "fine pores in the form of undercut" as used herein means a pore having an internal cavity larger than the pore inlet portion. The fine pores as defined above are formed by blowing fine particles of solids such as carborundum or silica entrained with pressurized fluid against the support base and then immersing the resulting scarred base into an oxidizing solution.

DESCRIPTION OF THE INVENTION

Figure 1:
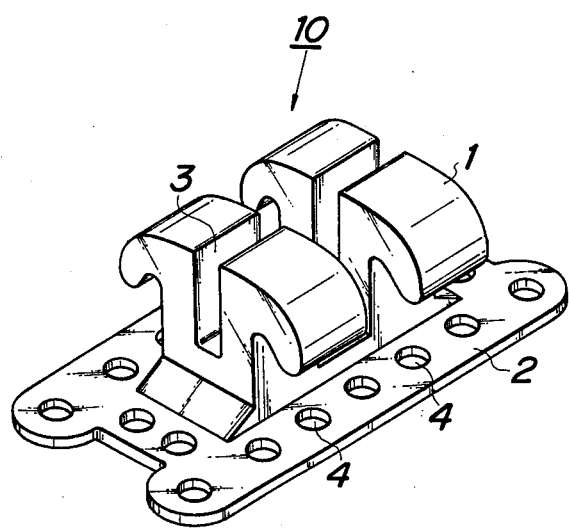
FIG. 1 is a perspective view schematically illustrating the metal bracket according to the present invention.

Referring to FIG. 1 of the accompanying drawings, a metal bracket according to the present invention is shown generally at 10. The metal bracket 10 comprises a bracket body 1 and a support base 2. The bracket body 1 has a groove 3 for receiving a wire (not shown) which transmits orthodontic force to the tooth. If desired, a plurality of through-pores 4 may be provided at the periphery of the support base 2. In this case, additional adhesion is provided between the base 2 and the tooth since the adhesive as applied to the base 2 partly comes out through the through-pores 4 and solidifies on the surface of the base 2.

Although the body 1 and the base 2 may be made of any metal unless they become rusty, stainless steel is preferred since they are relatively cheap and workable.

In order to form undercut fine pores in the base 2 according to the present invention, the support base 2 is firstly subjected to what is called a sand-blasting treatment. That is, the reverse side of the base is treated by blowing fine particles of silica or carborundum entrained with a pressurized fluid such as pressurized air. The scarred base 2 thus obtained is then subjected to an etching process. The etching process is effected by immersing the base 2 into an oxidizing solution. Any oxidizing solution for use in etching process may be utilized. The oxidizing solution includes, for instance, a solution of ferric chloride and a solution of potassium bichromate.

After the two-step treatment fine pores having internal cavities larger than the pore inlet portions are formed in the support base 2. Then the support base 2 is secured to the bracket body 1 by any known method for metal-to-metal bonding.

An adhesive for dental use is applied to the back of the base 2. The adhesive goes through the pore inlet portions into the internal cavities and solidifies. The solidified adhesive in the cavities serve as a stopper, thus preventing the metal bracket from being detached off the tooth. The bracket according to the present invention is thus fit good for long usage.

The following Examples are provided for further illustrating the invention.

EXAMPLE

Three samples of stainless steel discs each having a thickness of 0.3 mm and a diameter or 6 mm were treated as follows:

(Sample 1)

Figure 2:
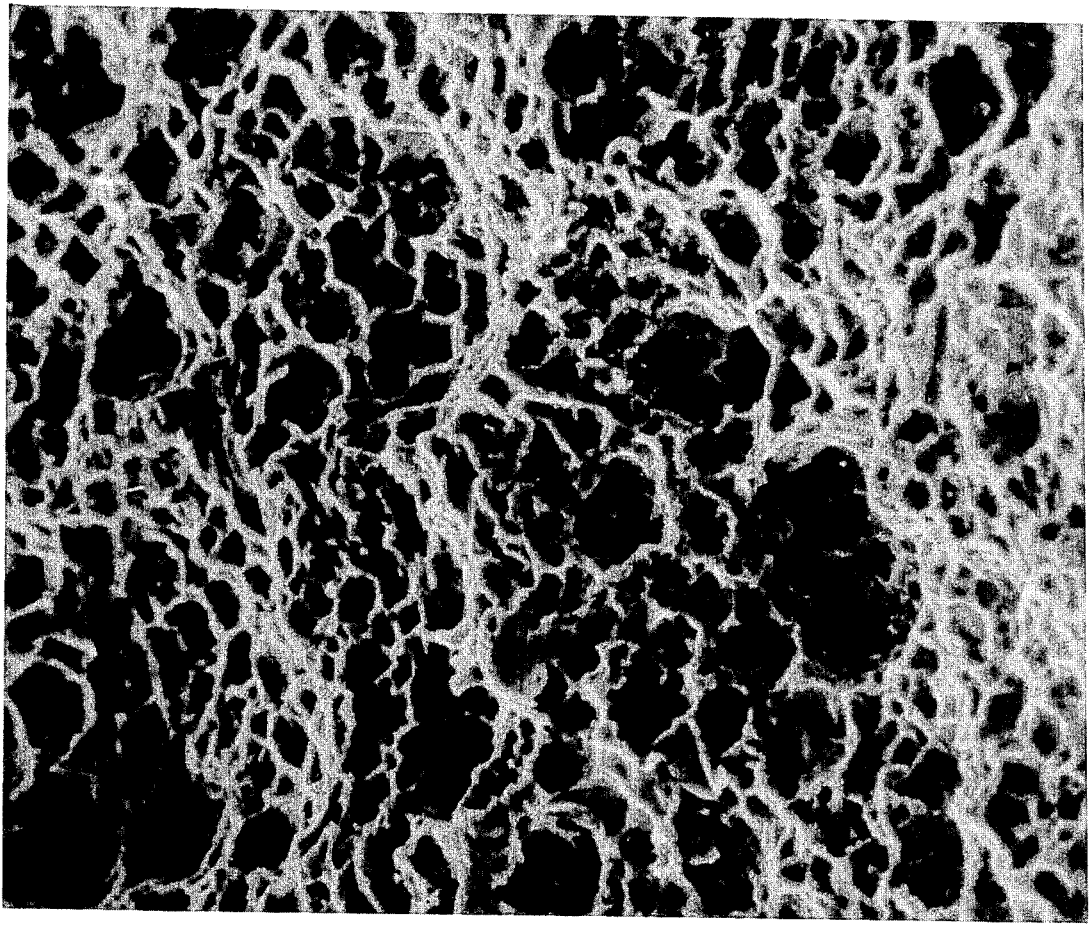
FIG. 2 is an electron microscopic photograph showing the back side of the support base according to the present invention.

Sample 1 was subjected to a sand-blasting treatment. Namely, particles of silica (40 mesh) were blown against the disc with pressurized air. Then the disc was immersed into a solution of ferric chloride (Baume 40°) at 14° – 15° C for 30 minutes, after which the disc was washed with water. The treatment was repeated six times and obtained undercut fine pores having an average depth of 0.05 mm. Electron microscopic photograph in FIG. 2 (Magnification of 1000) clearly shows undercut structure of fine pores made according to the present invention.

(Sample 2)

Figure 3:
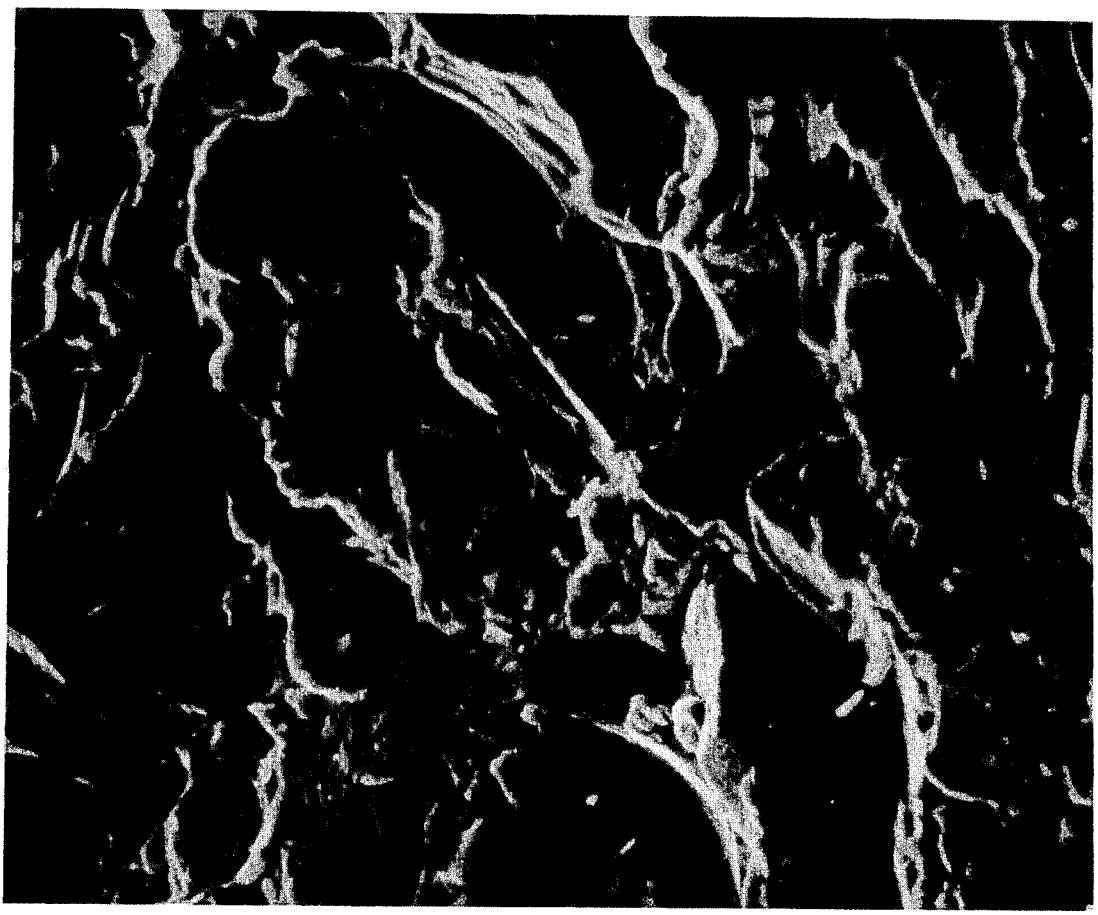
FIG. 3 is an electron microscopic photograph showing the back side of the support base treated by blowing with pressurized air fine particles of silica.

For comparison, the sand-blasting treatment mentioned in Sample 1 was only repeated except that the sample was scarred to form concaves of 0.05 mm in depth. FIG. 3 (Magnification of 1000) indicated that only by the sand-blasting treatment undercut structure was not formed.

(Sample 3)

Figure 4:
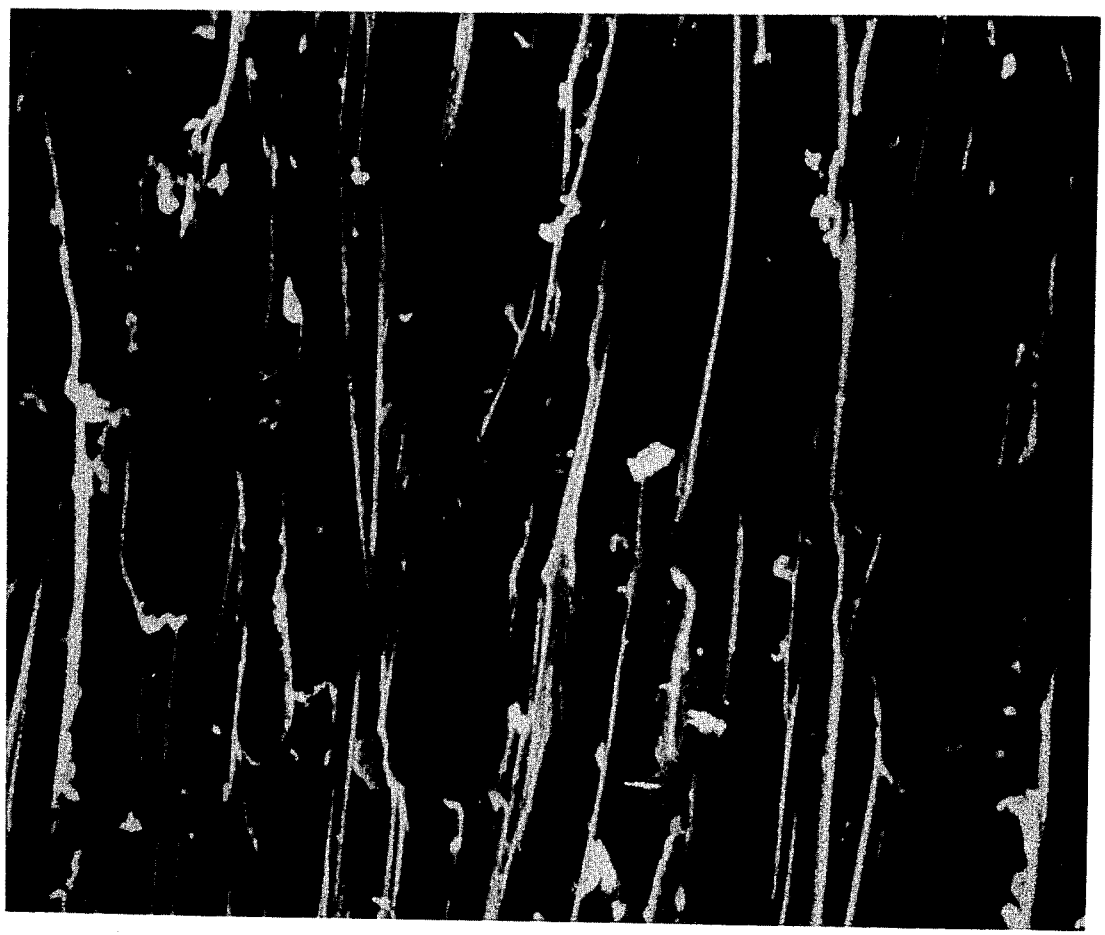
FIG. 4 is an electron microscopic photograph showing the back side of the support base treated by means of a rotating grinder.

Sample 3 was cut by means of a rotating grinder (diameter of 1cm) having carborundum surface at rotating speed of 1000 rpm until scratches of 0.05 mm in depth were obtained. FIG. 4 illustrates scraches thus formed. (Electron Microscopic photograph X 1000)

For the purpose of comparison a metallic net made by knitting stainless steel wires each having a diameter of 0.15 mm was used as Sample 4. The net of this type is utilized as a support base in the known type of the metal bracket. For the same purpose a support base (Diameter 6 mm, thickness 0.3 mm) for use in the known type of the metal bracket having a plurality of through-pores throughout the base was used as Sample 5.

An adhesive containing polymethyl methacrylate, methamethyl acrylate and tri-n-butyl boron as a catalyst was brushed on the surface of the samples 1 to 5, respectively and secured on the end face of an acryl resin stick having a diameter of 6 mm. The discs were left as they were for 24 hours at room termperature.

The resistant force against peeling the samples was determined using Universal Tensile Testing Instruments (Toyo Baldwin Co., Ltd.).

The results are shown in the following Table.

Table

| Sample | Resistant force against peeling (Kg/cm$^2$) |
| --- | --- |
| 1 | 67.7 |
| 2 | 57.5 |
| 3 | 25.8 |
| 4 | 57.8 |
| 5 | 57.1 |

While the present invention has been described with particular reference to the Example, it is to be noted that various modifications and variations may be made without departing from the essential spirit and scope of the invention. It is intended to include all such variations and modifications.

What is claimed is:

1. A metal bracket for use in orthodontic treatment which comprises a bracket body for receiving and securing a wire which transmits orthodontic force to the tooth and a support base for supporting said bracket body and which is adhered to the tooth, a plurality of fine pores in the form of undercut pores being formed in the support base by blowing fine particles of solids entrained in a pressurized fluid against the support base and then immersing the resulting scarred base in an oxidizing solution.

2. The metal bracket as claimed in claim 1 wherein a plurality of through-pores are provided along the periphery of said support base.

3. The metal bracket as claimed in claim 1 wherein said solids are selected from carborundum and silica.

4. The metal bracket as claimed in claim 1 wherein said oxidizing solution is a solution of ferric chloride.

* * * * *